United States Patent
Cuellar Soares et al.

(10) Patent No.: US 10,494,653 B2
(45) Date of Patent: Dec. 3, 2019

(54) PROCESS FOR THE RECOVERY OF LIPIDS OR HYDROCARBONS

(71) Applicant: Technische Universiteit Delft, Delft (NL)

(72) Inventors: Maria Claudia Cuellar Soares, Delft (NL); Lucas Antonius Maria van der Wielen, Delft (NL); Arjan Sebastiaan Heeres, Delft (NL)

(73) Assignee: DELFT ADVANCED BIOFUELS B.V., Delft (NL)

( * ) Notice: Subject to any disclaimer, the term of this patent is extended or adjusted under 35 U.S.C. 154(b) by 79 days.

(21) Appl. No.: 15/121,924

(22) PCT Filed: Feb. 25, 2015

(86) PCT No.: PCT/NL2015/050117
§ 371 (c)(1),
(2) Date: Aug. 26, 2016

(87) PCT Pub. No.: WO2015/130167
PCT Pub. Date: Sep. 3, 2015

(65) Prior Publication Data
US 2017/0073710 A1    Mar. 16, 2017

(30) Foreign Application Priority Data

Feb. 28, 2014 (NL) .................................... 2012334

(51) Int. Cl.
*C12P 7/64* (2006.01)
*C12P 5/00* (2006.01)

(52) U.S. Cl.
CPC .. *C12P 7/64* (2013.01); *C12P 5/00* (2013.01)

(58) Field of Classification Search
None
See application file for complete search history.

(56) References Cited

U.S. PATENT DOCUMENTS

| 7,659,097 B2 | 2/2010 | Renninger et al. |
| 7,960,574 B1 | 6/2011 | Dickey et al. |
| 2009/0029445 A1 | 1/2009 | Eckelberry et al. |
| 2012/0129244 A1 | 5/2012 | Green et al. |

FOREIGN PATENT DOCUMENTS

| CN | 102449155 A | 5/2012 |
| CN | 103080305 A | 5/2013 |
| EP | 2196539 A1 | 6/2010 |
| JP | 2012523849 A | 10/2012 |
| WO | 2007139924 A2 | 12/2007 |
| WO | 2008113041 A2 | 9/2008 |
| WO | 2010123903 A1 | 10/2010 |
| WO | 2011157848 A1 | 12/2011 |
| WO | 2012024186 A1 | 2/2012 |

OTHER PUBLICATIONS

Liu et al. Fatty acid production in genetically modified cyanobacteria. PNAS, Apr. 26, 2011, vol. 108(17), 6899-6904.*
Cardona et al. Fuel ethanol production: Process design trends and integration opportunities., Bioresource Technology 98 (2007): 2415-2457, Review.*
International Search Report for corresponding Int'l Pat. Appl. No. PCT/NL2015/050117, dated May 21, 2015, 3 pages.
Chinese Office Action dated Feb. 25, 2019 corresponding to Chinese Patent Application No. 201580022544.0.
Japanese Office Action dated Jan. 8, 2019 corresponding to Japanese Application No. 2016-554392.

* cited by examiner

*Primary Examiner* — Iqbal H Chowdhury
(74) *Attorney, Agent, or Firm* — Tarolli, Sundheim, Covell & Tummino LLP

(57) ABSTRACT

The invention is directed to a method for recovering a lipid or hydrocarbon from a fermentation mixture, comprising the steps of—providing a fermentation mixture wherein the lipid or hydrocarbon is produced by microbial fermentation in a fermentation vessel, which mixture comprises an aqueous phase and a liquid product phase, wherein the liquid product phase comprises the lipid or hydrocarbon; and—feeding at least part of the aqueous phase and part of the liquid product phase to a second vessel, thereby forming a second mixture; and—promoting phase-separation of the aqueous and product phase by injecting a gas into the second mixture, thereby separating the product phase from the aqueous phase; and—collecting the product phase comprising the lipid or hydrocarbon.

24 Claims, 4 Drawing Sheets

PROCESS FOR THE RECOVERY OF LIPIDS OR HYDROCARBONS

CROSS-REFERENCE TO RELATED APPLICATIONS

This application is the U.S. national phase entry of PCT/NL2015/050117, with an international filing date of Feb. 25, 2015, which claims priority to and the benefit of NL2012334, filed on Feb. 28, 2014, the contents of which are hereby incorporated by reference in their entirety.

FIELD OF INVENTION

The invention is directed to a method for recovering a liquid lipid or hydrocarbon from a fermentation mixture.

BACKGROUND OF THE INVENTION

It is known in the art to produce liquid hydrocarbon or lipid by fermentation. In such a fermentation process, microorganisms are used to convert a suitable substrate into hydrocarbon, lipid or a mixture thereof. Such microbial production of hydrocarbon or lipid is for example used to produce biofuels. Furthermore, chemical intermediates and flavour or fragrance compounds may be produced in this way.

The fermentation mixture obtained by the fermentation process is a complex mixture comprising micro-organisms, substrate, nutrient, the liquid fermentation product (e.g. hydrocarbon or lipid) and the gaseous fermentation product (i.e. fermentation gas). The mixture is a four phase (S-G-L-L) mixture: microbial cells (solid), fermentation gas and/or other gases (gas), aqueous medium (liquid) and the hydrocarbon or lipid (liquid).

A problem encountered in the microbial production of hydrocarbon or lipid by fermentation is that it is difficult to separate the produced hydrocarbons and lipids from the complex fermentation mixture.

Separation of the hydrocarbon and lipid generally relies on the low water-miscibility of the lipids or hydrocarbon with the aqueous medium, as is also described in the following prior art.

EP 2 196 539 describes the use of different solid-liquid-liquid separation techniques to separate the lipid and hydrocarbon biofuels (BHC) from a fermentation mixture. Preferred steps for this include the use of flotation of the BHC using dissolved carbon dioxide and other components in the fermentation gas in combination with a venturi type device (or other pressure reduction devices) or the use of hydrocyclones. No gas is actively injected into the reactor.

WO 2007/139924 is directed to a method for producing and separating bio-organic compounds in a two-phase system, which system comprises an aqueous medium with host cells as a first layer and a liquid organic second phase comprising the bio-organic compound produced by the host cells. It mentions the production of gases such as carbon dioxide during or after the fermentation process, which may be vented off using a gas outlet. Many possible variants of the production method are described, including batch, continuous, fed-batch or semi-continuous fermentation processes and aerobic or anaerobic host cells.

WO 2012/024186 is directed to a more specific purification process wherein a composition comprising a surfactant, host cells and a bio-organic compound is heated from below to above a phase inversion temperature of the composition, thereby destabilizing the emulsion.

WO 2010/123903, US 2009/029445 and US 2012/129244 describe processes for harvesting the intracellular components from an aqueous solution comprising microorganisms, in particular algae. These processes include rupturing the cell walls of the microorganisms in order to release the intracellular components into the aqueous solution. The intracellular components can be separated from the solution by applying microbubbles and forming a foam layer, such that the intracellular components attach to the microbubbles and float upwards toward the surface of the aqueous solution. The intracellular components are recovered by separating the foam from the aqueous solution.

U.S. Pat. No. 7,960,574B1 describes a method of separating oil from oil-containing seeds, comprising aerating an aqueous dispersion of germ particles of oil-containing seeds. The aeration results in bubbles to which the oil adheres and the bubbles form a foam at the upper surface of the dispersion. The oil is recovered by separating the foam from the dispersion.

A disadvantage of WO 2010/123903, US 2009/029445, US 2012/129244 and U.S. Pat. No. 7,960,574B1 is that the product is obtained as part of a foam, such that further phase-separation (e.g. decanting, centrifugation) is still required in order to isolate the product.

It is an object of the invention to recover the liquid fermentation product from the fermentation mixture in a more efficient way by enhancing separation of the liquid product and the aqueous medium of the fermentation mixture.

SUMMARY OF THE INVENTION

This object is met by providing a method for recovering a lipid or hydrocarbon from a fermentation mixture, comprising the steps of providing a fermentation mixture wherein the lipid or hydrocarbon is produced by microbial fermentation in a fermentation vessel (e.g. a first vessel or a first compartment of a fermentation reactor), which mixture comprises an aqueous phase and a liquid product phase, wherein the liquid product phase comprises the lipid or hydrocarbon; and feeding at least part of the aqueous phase and part of the liquid product phase to a second vessel (e.g. a separate second vessel or a second compartment of a fermentation reactor), thereby forming a second mixture; and promoting phase-separation of the aqueous and product phase by injecting a gas into the second mixture, thereby separating the product phase from the aqueous phase; and collecting the product phase comprising the lipid or hydrocarbon.

Preferably, the fermentation vessel and second vessel are separate compartments in a fermentation reactor (preferably a gas-lift reactor). In this case, the fermentation vessel is referred to as the first compartment and the second vessel as the second compartment. Alternatively, the fermentation vessel and second vessel may be separate reactors. The conditions in the fermentation vessel are suitable for fermentation. The conditions in the second vessel are suitable for phase-separation (and are generally different from the fermentation conditions).

DETAILED DESCRIPTION OF THE INVENTION

Figure 1:
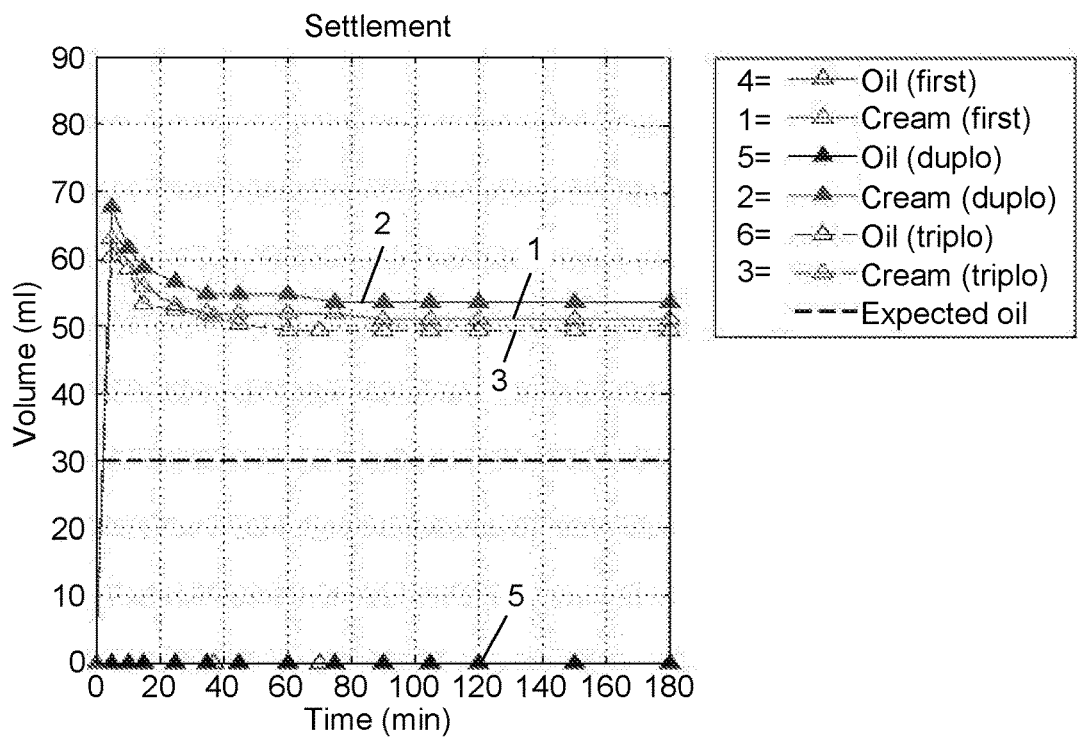
FIG. 1 is a graph showing the cream and oil development in time.

The inventors found that by injecting gas into the second mixture, phase-separation of the aqueous medium and liquid product phase are enhanced. By active injection of the gas, the phases can be separated in a more controlled manner. This allows for a more efficient phase-separation, for example by avoiding or reducing cream formation in the fermentation vessel and/or destabilizing an emulsion if formed. In particular, by controlling the gas flow rate and/or the size of the gas bubbles of the injected gas, the liquid product phase can be more efficiently separated and recovered from the fermentation mixture.

Without wishing to be bound by any theory, the inventors expect that certain compounds produced by the micro-organism during fermentation act as surfactants. These surfactants are possibly removed by injecting gas into the liquid mixture (i.e. into the mixture of the aqueous phase and the liquid product phase), thereby resulting in the separation of the product phase and the aqueous phase. An alternative mechanism through which the invention may work is that droplets of liquid product attach to the injected gas bubbles in such a way that coalescence of the product phase is enhanced.

As mentioned above, a further advantage of the invention is that the formation of a cream layer in the second vessel may be reduced or even prevented.

When conducting fermentation in a column type vessel or reactor, different layers will generally form. Since generally vigorous mixing is conducted in the fermentation vessel, such layers will generally only form in the second vessel. Thus, the second mixture may comprise one or more layers, as described below. First, a foam layer may be formed at the top of the column, caused by one or more of vigorous mixing of the fermentation mixture, injection of oxygen containing gas (in case of aerobic fermentation) and the production of fermentation gas. Such a foam layer comprises a large amount of bubbles such that the density is generally lower than 500 kg/m$^3$. Furthermore, a cream layer may form. The cream layer is an emulsion of the liquid fermentation product (lipid or hydrocarbon) and water. This layer will have a higher density than the foam layer, typically of about 600 to 980 kg/m$^3$. The foam layer and cream layer will generally form on top of the aqueous phase, which may be considered the bottom layer. The aqueous layer typically has a density of about 1000 kg/m$^3$, e.g. above 990 kg/m$^3$)

A cream layer may for example form when (part of the) fermentation mixture is settled, e.g. after gravity settling or centrifugation. It may also sometimes spontaneously form under fermentation conditions. A cream layer typically forms between the aqueous layer (bottom layer—aqueous phase) and the oil layer (upper layer—product phase). When formed, the cream layer will generally have a relatively high amount of liquid product compared to the content of the rest of the fermentation mixture. However, the cream comprises large droplets of liquid product which cannot coalesce any further. To obtain the product from the cream layer, the cream needs to 'broken', such that further coalescence can occur. The inventors found that this can be achieved by injecting gas according to the method of the invention. Accordingly, a fourth layer will form: the product layer. The composition of the product layer generally corresponds to the composition of the product phase in the fermentation mixture. This layer may comprise at least 90 wt. %, more preferably at least 95 wt. % of the liquid product (hydrocarbon or lipid). In case an organic solvent is present in the product phase for extracting the liquid fermentation product, at least 90 wt. %, preferably at least 95 wt. % of the product layer will consist of an organic solution comprising the liquid fermentation product and possible hydrocarbons not produced in the fermentation. Due to the high amount of liquid product, the density of this layer will be lower than that of the cream layer (if formed), but still higher than that of the foam layer.

Furthermore, the different layers can be distinguished by their oil volume fraction. The volume fraction of oil will be highest in the product phase. The product layer may have a volume fraction of oil that lies between 0.9 and 1.0 The cream layer may have a volume fraction of oil that lies between 0.5 and 0.9 The foam layer may have a volume fraction of oil that lies between 0.01 and 0.4. The term "oil volume fraction" refers to the total amount of liquid fermentation product present in the layer (in particular, the total amount of the lipid and hydrocarbon produced by the micro-organisms present in the layer), divided by the total volume of the layer.

Phase-separation according to the invention may be promoted by induced gas flotation (IGF). Using this technique, gas bubbles are actively injected into the liquid.

In particular, phase-separation may be promoted by controlling the superficial gas velocity.

The superficial gas velocity is defined as the total volume of gas (e.g. in cm$^3$) that passes through a cross-sectional area of the vessel (e.g. in cm$^2$) over a certain amount of time (e.g. per second). Preferably, the gas is injected in order to obtain a superficial gas velocity in the second vessel in the range of 0.01-2.0 cm/s, more preferably 0.05-1.5 cm/s, even more preferably 0.1-1.0 cm/s. Such values for the superficial gas velocity are considerably lower than the values typically used in aerobic fermentation. In case of aerobic fermentation, the oxidizing gas is fed at a higher gas velocity in order to suitably provide the micro-organisms with sufficient oxygen.

The superficial gas velocity is measured at the point of injection of the gas. This means that the cross-sectional area of the vessel is determined at the height of the vessel where the gas is injected. In case of multiple points of injection, the superficial gas velocity should be within the above-specified range at least one of the multiple injection points. The cross-sectional area is typically measured perpendicular to the direction of the gas flow. In case the vessel is a column or column type vessel, the cross-sectional area is typically measured perpendicular to the length of the column. In case the cross-sectional area of the vessel is about uniform (for example in a column type vessel), the superficial gas velocity may be about the same throughout the entire vessel. A certain superficial gas velocity can be achieved by adjusting the flow rate of the gas to the geometry of the vessel. For example, one can first determine the cross-sectional area of the vessel used and then adjust the flow rate of the gas (i.e. the volume of gas injected per unit time) in order to achieve the desired superficial gas velocity.

The gas used in the invention is typically injected in the form of gas bubbles. The inventors expect that the size of the bubbles may further enhance the efficiency and/or rate of phase-separation. For example, stronger phase-separation may under certain conditions be achieved by using a larger bubble size.

The gas may be injected into the second mixture by any suitable way known in the art. Typically, gas bubbles are injected into the liquid mixture. The gas may be advantageously distributed through a sparger and/or sintered plate in order to obtain the desired bubble size and/or flow rate. In order to inject the gas efficiently to the liquid mixture, the gas is typically fed to the reaction vessel or, in case a second vessel is used, to the second vessel.

According to the invention, the gas is injected into the liquid mixture, i.e. into a mixture of the aqueous phase and the liquid product phase. The liquid mixture corresponds to the second mixture. The liquid mixture may be an emulsion, wherein the liquid product phase is dispersed in the aqueous phase. The liquid mixture may also comprise a cream comprising liquid product.

The gas may be a non-oxidizing gas, such as an inert gas or a fermentation gas. The inert gas may for example be a noble gas, nitrogen or $CO_2$. The gas may also be a fermentation gas. For example, the fermentation gas formed by fermentation may be collected and injected into the second mixture. In this case, the fermentation gas is typically first separated from the fermentation mixture and subsequently recycled by feeding it to the second vessel.

Alternatively, the gas may be an oxidizing gas, such as air. For example air enriched in oxygen may be used. Such enriched air is also used in aerobic fermentation to provide oxygen to micro-organisms.

According to the process of the invention, gas is injected into the second mixture. However, gas may also be introduced into the fermentation mixture. For example, the fermentation mixture may be mixed by a static mixer. Furthermore, in case of aerobic fermentation, oxygen containing gas (such as air) may be introduced in the fermentation mixture to provide the micro-organisms with oxygen. Furthermore, gas may be produced in the fermentation mixture by the micro-organisms as a fermentation product (e.g. fermentation gas). Despite the introduction of such gas in the fermentation mixture, this will generally not result in phase separation of the product phase, let alone enhance coalescence of the lipid and hydrocarbon droplets in the fermentation mixture. The conditions in the fermentation vessel are simply not suitable for such phase-separation. Rather, the conditions are suitable or optimized for fermentation. For example, the superficial gas velocity of the gas injected or produced in the first vessel will generally be higher in the fermentation vessel than in the second vessel (typically above 1.5 cm/s or even above 2.0 cm/s). In view of the conditions in the fermentation vessel, at least part of the aqueous phase and part of the liquid product phase are transferred to a second vessel, wherein the conditions can be chosen to be suitable for phase-separation.

Accordingly, at least part of the aqueous phase and part of the liquid product phase are fed to a second vessel, thereby forming a second mixture. This may simply be done by feeding at least part of the fermentation mixture to the second vessel. Any solid matter ending up in the second vessel may be recycled to the fermentation vessel. For example, micro-organisms in the second vessel may be recycled to the fermentation vessel. In particular, at least part of the liquid mixture (as defined above) may be fed to the second vessel and form the second mixture. The second mixture thus comprises a mixture of an aqueous phase and the liquid product phase (e.g. in the form of an emulsion). The second mixture may further comprise a cream (which may e.g. be formed in the fermentation vessel or in the second vessel). When a feeding step is used as described above, the gas will be injected into the second mixture, instead or in addition to injection of gas into the fermentation mixture.

The conditions in the second vessel should be suitable for promoting phase-separation. No fermentation will generally occur in the second vessel. Accordingly, the conditions in the second vessel may be different from the conditions in the fermentation vessel. First, the superficial gas velocity in the second vessel may be chosen differently. Also, a different temperature and/or pressure may be used in the second vessel. Further, it is desirable that no mixing is conducted in the second vessel, because this may negatively influence coalescence and phase-separation.

Although the conditions in the second vessel may not be optimized for fermentation, it is still undesirable when micro-organisms are disrupted in this stage. The presence of the micro-organisms' intracellular products (in particular cell debris) in the second mixture was found to interfere with the phase-separation and formation of the product layer, as shown in Example 5. Therefore, it is undesirable if such intracellular products are present in the second mixture. Intracellular products as used herein may refer to the material obtained by disruption of micro-organisms, in particular by disruption of the micro-organisms that produce the fermentation product. Disruption may refer to disruption by cell lysis or physical, chemical and/or enzymatic disruption. Intracellular products include cell debris, which includes the solid intracellular products, such as cell wall fragments. Accordingly, the second mixture preferably comprises less than 5 wt. % intracellular products, more preferably less than 1 wt. %, even more preferably less than 0.1 wt. %, even more preferably no intracellular products at all. In particular, the second mixture comprises an amount of cell debris that is below these values.

Preferably, micro-organisms in the second vessel are recycled by feeding them back to the fermentation vessel. Accordingly, preferably at least 50 wt. %, more preferably at least 75 wt %, even more preferably at least 90 wt. %, even more preferably at least 95 wt. % of the biomass present in the second vessel corresponds to the mass of intact micro-organisms. The biomass as used herein refers to biomass originating from the micro-organisms in the fermentation mixture other than the lipids or hydrocarbons produced by the micro-organisms, expressed in dry weight. Feeding back intact micro-organisms can be achieved by configuring the fermentation vessel and second vessel such that the micro-organisms can be quickly fed back to the fermentation vessel and only stay in the second vessel for a short duration. This can be achieved by integrating the fermentation vessel and the second vessel. An example of such an integrated system is a fermentation reactor with two compartments, wherein fermentation is conducted in the first compartment and phase-separation in the second compartment.

After fermentation (but before injecting the gas), at least part of the fermentation mixture may be subjected to a settling step, e.g. a gravity settling or centrifugation step. Such a step can be used to increase the content of liquid product in the fermentation mixture. Due to the difference in density between the liquid product and water, one can separate off part of the fermentation mixture with a higher content of liquid product. Accordingly, an enriched liquid mixture is obtained, i.e. a liquid mixture that is enriched in the liquid product. For example, the enriched fermentation mixture may be used as the second mixture and fed to the second vessel where gas injection will take place. In case the settling step is conducted on only a part of the fermentation mixture (e.g. the second mixture), it is typically done in a vessel other than the fermentation vessel (i.e. in a settler). For example, the second mixture may be subjected to settling, either before or after feeding it to the second vessel. Since any cream formation that may arise can be easily processed with the injection of gas as described above, a settling step can thus be suitably used as a process step to obtain the liquid product from a fermentation mixture.

Solid matter such as micro-organisms may be transferred from the fermentation vessel (e.g. the first compartment of the fermentation reactor) to the second vessel (e.g. the second compartment of the fermentation reactor). In case of a continuous process, solid matter is typically fed back to the fermentation vessel. Further, in the second vessel, the second mixture may be formed by letting the part of the liquid product phase and part of the aqueous phase settle. This may result in the formation of cream or an emulsion. Since the fermentation mixture generally needs to be mixed (e.g. by stirring or by addition of gas), such formation does not always occur to the fermentation mixture.

The second vessel and the fermentation vessel may optionally be connected, such that the fermentation mixture and the second mixture are in direct contact with each other. Accordingly, part of the liquid mixture may be continuously fed to the second vessel.

The fermentation vessel and second vessel may be separate compartments in a fermentation reactor. Alternatively, the fermentation vessel and second vessel are separate reactors.

More specific details on the general set-up of the fermentation vessel and conditions under which the process is conducted are described below.

The fermentation vessel comprises an outlet through which the at least part of the aqueous phase and part of the liquid product phase may be transferred to the second vessel. Preferably, no gas bubbles are present in the at least part of the aqueous phase and part of the liquid product.

The fermentation vessel may further comprise a gas outlet, which allows gas bubbles to leave the fermentation vessel. Such a gas outlet may ensure that gas bubbles introduced (e.g. injected or formed (e.g. fermentation gas) in the fermentation mixture do not directly enter the second vessel. This would be undesirable, because they may have a negative effect on coalescence and phase-separation.

The second vessel may further comprise an outlet through which micro-organisms can be recycled to the fermentation vessel.

In case the fermentation vessel and second vessel are separate compartments in a fermentation reactor. The first compartment in the fermentation reactor is the compartment wherein fermentation takes place. The first compartment comprises the majority of the micro-organisms (over 50 wt. %, typically over 80 wt. %). The second compartment is the compartment of the fermentation reactor wherein phase-separation is promoted. The fermentation reactor may be an gas-lift reactor or a bubble column reactor with two compartments. Preferably, the fermentation reactor is a gas-lift reactor. The gas-lift reactor may have an internal recirculation, for example using a draft tube, or an external recirculation.

In case of two separate reactors, the fermentation vessel may for example be a fermentation reactor (e.g. a bubble column reactor or gas-lift reactor), while the second vessel is a separating reactor, such as a gas-liquid reactor (e.g. a bubble column reactor) or an induced gas flotation reactor (e.g. an induced gas flotation separator).

Preferably, the fermentation vessel and/or second vessel is a column type vessel or reactor, for example a column type fermentation reactor. The process is typically conducted in up-flow, which means that at least part of the aqueous phase of the fermentation mixture moves in upward direction in the fermentation vessel. In case the fermentation vessel and second vessel are separate compartments in a fermentation reactor, the fermentation reactor will be configured such that the aqueous phase and the product phase will flow from the first compartment (fermentation vessel) into the second compartment (second vessel). Further, there may be recirculation over the fermentation vessel. This may either be an internal recirculation, for example using a draft tube, or an external recirculation.

The method of the invention can be conducted batch-wise, fed-batch-wise or continuously.

The fermentation vessel and second vessel may be operated at a pressure of between 1.0-1.2 bar, preferably at ambient pressure (about 1.0 bar). A temperature between 5 and 60° C., typically between 20 and 40° C. may be used. Low temperatures can be used as long as both the water and liquid product do not solidify. As described above, the temperature and pressure in the fermentation vessel and second vessel may be different, but they are generally chosen (independently from each other) within the above ranges.

As described above, the fermentation mixture typically comprises micro-organisms, a substrate and the fermentation products (hydrocarbon and/or lipids, fermentation gas).

The micro-organisms in the fermentation vessel are micro-organisms capable of producing hydrocarbon or lipid by fermentation. The fermentation mixture is therefore kept under conditions that are suitable for the micro-organisms to produce lipid or hydrocarbon. The conditions in the fermentation vessel may further be suitable for the micro-organisms in the fermentation mixture to grow and/or reproduce. It will thus be evident that the conditions are chosen such that no large amount of micro-organisms in the fermentation vessel are disrupted, damaged or inactivated in any other way such that they would no longer be capable of fermentation. Preferably, the fermentation mixture is mixed. Mixing may for example be conducted by a mixer and/or by addition of gas. Mixing gas may be achieved by injecting gas at relatively high superficial gas velocity. In order to produce heterogeneous mixing, gas is preferably added with a superficial gas velocity of above 1.5 cm/s or even above 2.0 cm/s.

The liquid product (lipid or hydrocarbon) is secreted into the fermentation mixture by living micro-organisms. The micro-organisms do not have to be harvested to obtain the lipid and hydrocarbon.

Suitable micro-organisms for fermentation are known in the art. Both anaerobic and aerobic micro-organisms may be used. The micro-organism may optionally be supported. Many possible hydrocarbons and lipids can currently be produced by micro-organisms which have been specifically developed for the production of biofuels. The most common groups of micro-organisms used are *Saccharomyces cerevi-*

*siae* and *E. coli*. Other examples of suitable micro-organisms are known from WO 2008/113041 (LS9), WO 2012/024186, WO 2007/139924, U.S. Pat. No. 7,659,097B2 and from Kalscheuer R, Sölting T and Steinbüchel A. 2006. Microdiesel: *Escherichia coli* engineered for fuel production. Microbiology 152: 2529-2536 or in Li Q, Du W and Liu D. 2008. Perspectives of microbial oils for biodiesel production. Applied Microbiology and Biotechnology 80: 749-756 or in Schirmer et al. 2010. Micorbial biosynthesis of alkanes. Science 329: 559-562 or in Ladygina et al. 2006. Process Biochemistry 41: 1001-1014. The specific aerobic and anaerobic bacteria for producing liquid organic products (e.g. hydrocarbons or biofuel) mentioned in these documents are incorporated herein by reference.

The micro-organisms can be freely suspended, immobilized, forming granules, forming flocs and the like. In this way the cell concentration in the reactor can be optimized and less surplus cell mass is produced. Additionally, separation of the cell mass may be enhanced.

The microbial fermentation is conducted under aerobic or anaerobic conditions.

The substrate present in the fermentation mixture is in general a bio-based feedstock, such as carbohydrates (e.g. sugars), starch and cellulose (or hydrolysates thereof). Other suitable feedstocks may be derived from glycerol, low cost biofuels (methanol, ethanol and the like), agro/forestry residuals, hydrolysates of agro/forestry residuals and gasified forms thereof (for example syngas).

These substrates are generally introduced into the fermentation vessel as an aqueous solution, either directly into the vessel or into the recycle flow, if present.

The fermentation mixture may also contain other (e.g. oxidized) products next to the liquid fermentation product, such as organic acids and polymers thereof (for example polyalkanoates).

The lipid or hydrocarbon recovered in the method of the invention can be any lipid or hydrocarbon that can be produced by aerobic or anaerobic fermentation using microorganisms. For example, the lipid or hydrocarbon may be a long chain lipid or fatty acid having e.g. at least eight carbon atoms. The lipid or hydrocarbon is in particular a liquid (for example an oil) at the fermentation conditions under which it is produced. The lipid or hydrocarbon is herein also referred to as the liquid fermentation product or simply the liquid product. This product formed may also be a mixture of one or more lipids and/or one or more hydrocarbons. When the liquid fermentation product is produced, it will form a liquid product phase in the fermentation mixture. The liquid product phase may mainly consist of the liquid fermentation product (e.g. consist of at least 75 wt. %, preferably at least 90 wt. % or even at least 95 wt. % of the product). However, the liquid product phase may also comprise an organic solvent or solution (e.g. for more than 50 wt. %), as explained for the product extraction embodiment below.

The product phase of the fermentation mixture may further comprise one or more organic solvents, for example alkanes or alkenes, preferably alkanes or alkenes having from 10 to 20 carbon atoms, such as dodecane, hexadecane or farnesene. The product phase may also comprise a mixture of multiple organic solvents, for example fuels such as diesel or kerosene. The product phase of the fermentation mixture may also comprise one or more hydrocarbons that are not produced in the fermentation, which may be dissolved in the organic solvent. Organic solvents may be used for product extraction during fermentation. In such an embodiment, the liquid fermentation product is extracted into the organic solvent, thereby forming an extract (typically in the form of droplets), which is an organic solution comprising the liquid fermentation product and the organic solvent. Such product extraction is well-known in the art and may for example be used to prevent product inhibition or to enrich an organic solvent with a liquid fermentation product. The skilled person will know how to conduct this extraction technique. Examples of a liquid fermentation products that may be extracted in such a way are mono and sesquiterpenes.

The droplets of the liquid fermentation product that is produced in the process of the invention may have varying sizes, ranging from small (<10 µm), medium (10-100 µm) or large (>100 µm). In case of product extraction, these droplet sizes correspond to the droplet size of the extract (i.e. the organic solution comprising the liquid fermentation product and the organic solvent).

The lipid or hydrocarbon is generally present in emulsified form, which may be stabilized by the presence of micro-organisms and other biological particles and molecules. Accordingly, the fermentation may comprise an emulsion of hydrocarbon and/or lipid in water.

The fermentation mixture in the fermentation vessel is typically mixed, e.g. by stirring and/or by gas sparging. In case the fermentation mixture is settled in the fermentation vessel, such mixing will of course no longer be conducted.

In the method of the invention a large amount of fermentation gas may be generated. The fermentation gas typically generates turbulent mixing and dispersion in the fermentation vessel and may provide a useful gas lift function in the vessel. Fermentation gas is commonly composed of mainly carbon dioxide (as the major gas component, e.g. at least 50 vol %). Typically, fermentation gas further comprises water vapour. It may further also comprise substantial amounts of methane.

The fermentation gas may under certain conditions also have a useful function in the separation of the liquid fermentation product from the fermentation mixture. However, a disadvantage of using fermentation gas for enhancing separation of the aqueous phase and the liquid product phase is that it cannot be accurately controlled. In particular, the bubble size and flow rate of the fermentation cannot be controlled. Generally, the fermentation gas is dissolved in the fermentation mixture and has a bubble size that is too small to efficiently separate the two liquid phases in the fermentation mixture. In contrast, the present invention provides for indirectly using the fermentation gas by first collecting the gas and then injecting it under the right conditions and velocity.

The liquid fermentation product may be collected from the second vessel by techniques known in the art, for example by decantation. The product layer can simply be tapped off or pumped out of the second vessel. In case the product was extracted into an organic solvent in the fermentation mixture, the liquid fermentation product will be collected as an organic solution.

The invention is further illustrated in the following Examples.

Example 1: Batch Oil Recovery

First, the fermentation mixture was prepared. Per batch 1.6 litre of 10% v/v hexadecane in water dispersion was prepared. All components were weighed before addition and added to a 2 L vessel containing a four-blade Rushton turbine and two baffles. The components were added in the following order:

| | | |
|---|---|---|
| 1. Milli-Q water | 1402.67 g | |
| 2. Wet baker's yeast | 53.33 g | |
| 3. Hexadecane | 123.68 g | |

The stirrer speed was set at N=900 RPM for t=180 minutes to mix the biomass and break the oil layer into small oil droplets. A cryostat was attached to keep the temperature constant at T=23° C. A thermometer was used to measure the temperature, placed in the therefore designated port of the fermentor lid.

At t=180 minutes the stirrer was stopped after which the lid was immediately removed and the dispersion poured into the glass columns.

After preparing the dispersion each column was filled with 300 ml of dispersion via a funnel. The glass columns had a sintered plate at the bottom (estimated bubble diameter=2-3 mm), internal diameter=37 mm and height (above the sintered plate)=645 mm. One column was used for a gravity settling experiment (Column I—settler) and one column for enhanced oil separation by the gas phase (Column II—second vessel).

Column II was connected to 0-10 l air/min mass flow controller. Air supply was switched on after filling the columns with 300 ml dispersion. The superficial gas velocity in the column was the range of 0.01-2 cm/s.

Volumes of the cream layer and clear oil layer were measured in time without cutting the air supply. Gas holdup in the column was measured at the end of each experiment by measuring the difference in volume of the cream and oil layer with and without gas supply. Measured volumes in time were corrected for this gas holdup.

Figure 2:
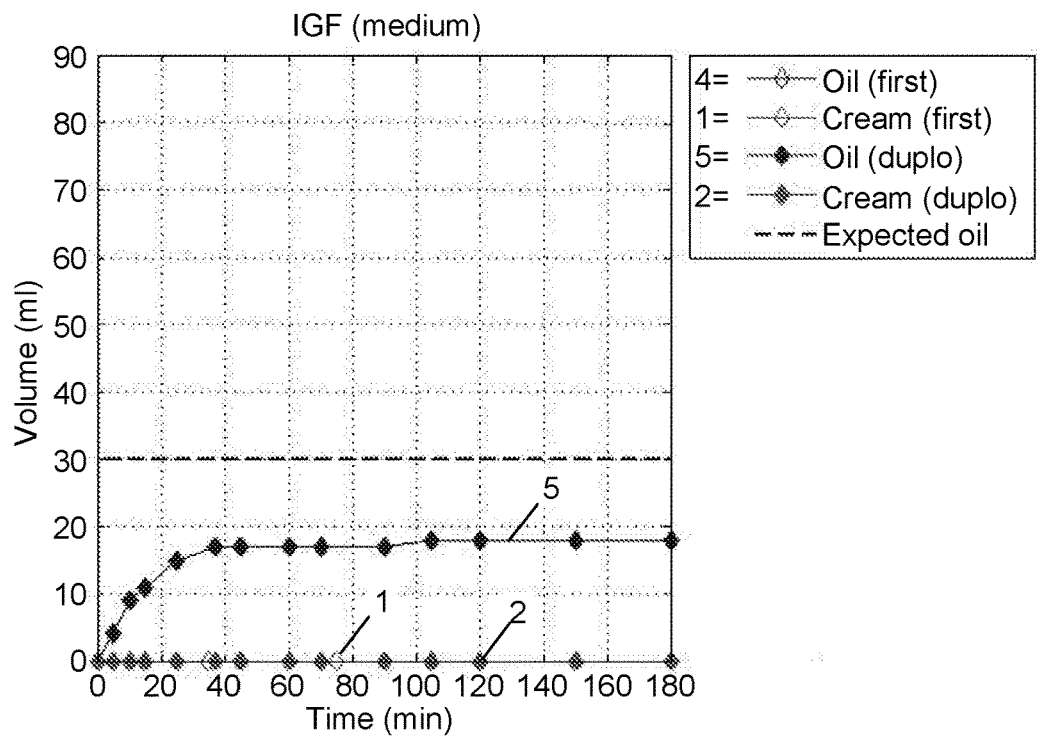
FIG. 2 is a graph showing the cream and oil development in time.

FIGS. 1 and 2 show the cream and oil development in time in both columns (left: column I, separation by gravity settling; right: column II, enhanced separation by gas phase). Clearly, the gas phase allows for directly recovering most of the oil as a separate oil layer (blue line in the graphs), in contrast to gravity separation, which yields oil droplets stabilized in a cream layer (red line in the graphs). Remarkably, there was no cream formation in column II.

Example 2: Continuous Oil Recovery

Figure 3:
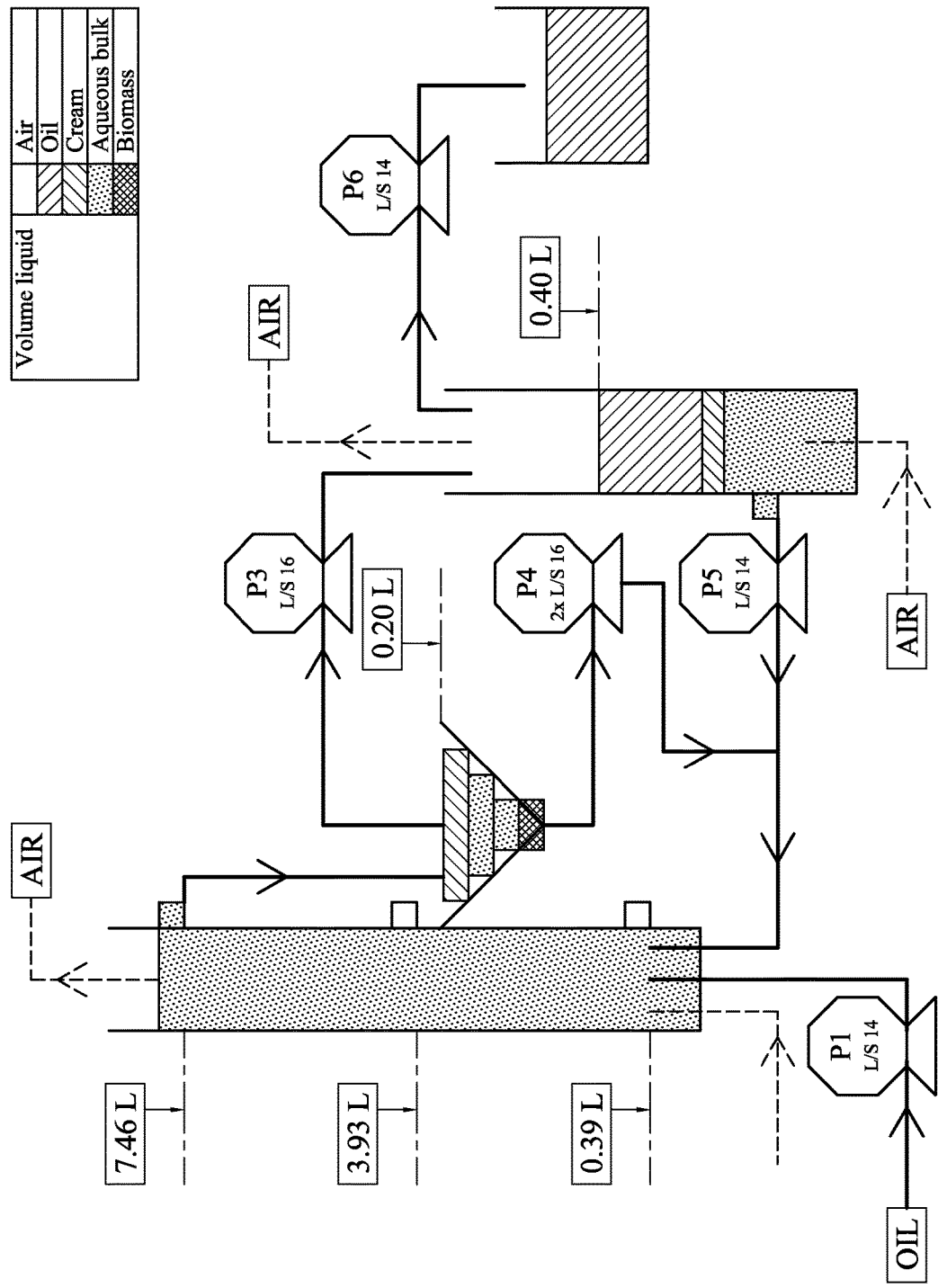
FIG. 3 is a schematic representation of the continuous set-up.

The continuous set-up consisted of a 8 L bubble column of 10 cm diameter for fermentation mixture preparation, a 0.5 L conical funnel as settler for obtaining a mixture with concentrated oil fraction (cream), a 0.5 L bubble column (such as column II in previous example—second vessel) for oil separation and a vessel for oil recovery. All flows between the vessels were controlled using Masterflex pumps, except for the overflow from the 8 L bubble column to the conical funnel. A schematic representation of the setup is shown in FIG. 3.

The start-up phase consisted of preparing a fermentation mixture of similar composition as above with 700 mL of hexadecane in the 8 L bubble column (fermentation vessel) by sparging compressed air at a superficial gas velocity of 3 cm/s for 6 hours. Subsequently, the conical funnel (settler) was filled, and after 5 minutes of settling the 0.5 L bubble column (second vessel) was filled in 1 hour and the recycle flow activated. Air was injected in the 0.5 L bubble column with a superficial gas velocity in the range of 0.01-2 cm/s. After approximately 2 hours, some clear oil was already recovered in vessel for oil recovery and the continuous operation mode was started by activating the fresh oil inflow.

300 mL of fresh oil were fed to the system in approximately 6 hours, while 285 mL of clear oil was recovered in the vessel for oil recovery, resulting in a 95% oil recovery yield on volume basis under continuous operation.

Example 3: Effect of Superficial Gas Velocity on Batch Oil Recovery

Figure 4:
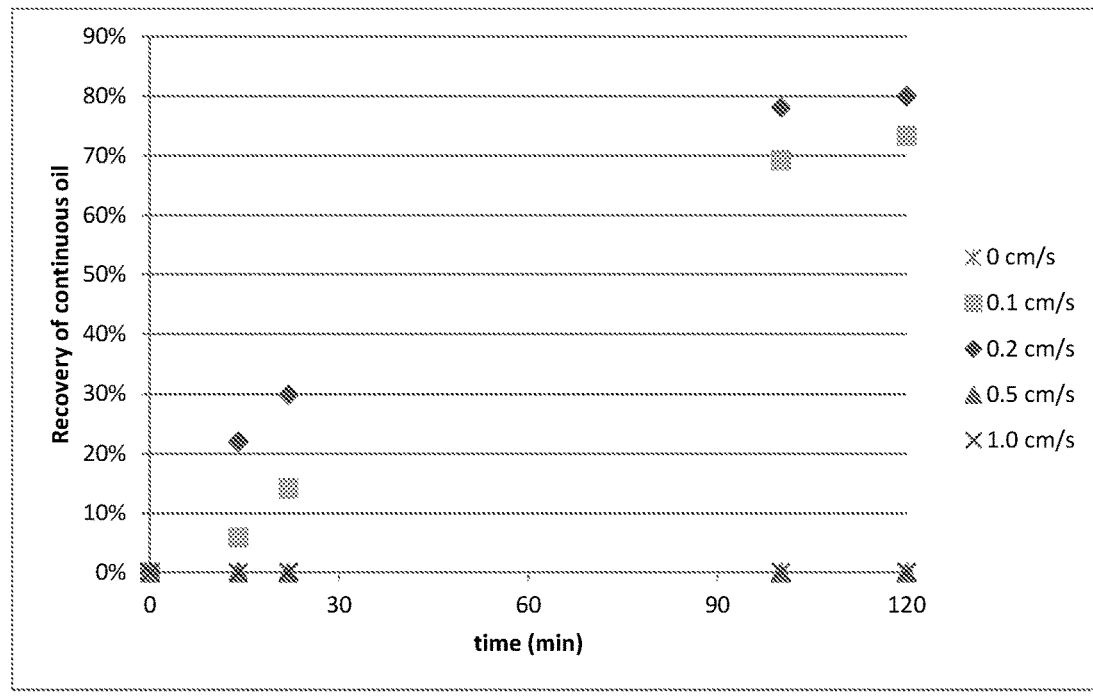
FIG. 4 is a graph showing the recovery of oil in the continuous oil layer over time.
Figure 5:
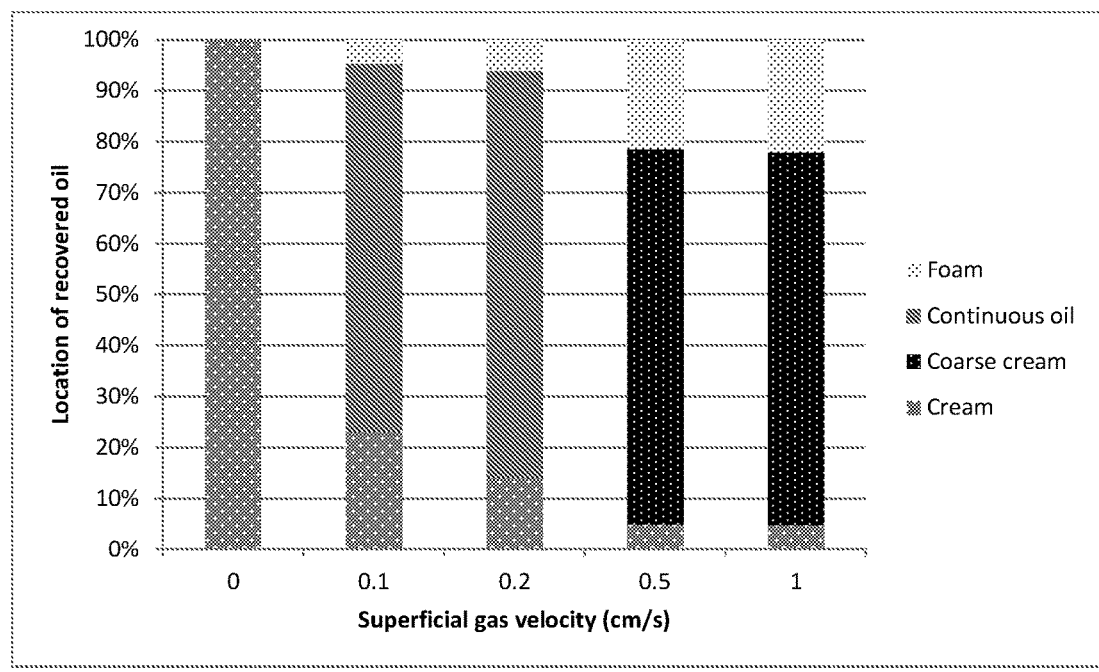
FIG. 5 is a graph showing the distribution of the oil over the different phases.

First, the fermentation mixture was prepared according to example 1. After preparing the dispersion, five glass columns with the same dimensions as in example 1 were filled with 300 mL of dispersion each. The five columns were operated with different superficial gas velocity (0, 0.1, 0.2, 0.5, 1.0 cm/s) for 2 hours. FIG. 4 shows the recovery of oil in the continuous oil layer over time for the four different columns. After the two hours of separation, the distribution of the oil over the different phases in the columns was determined, as shown in FIG. 5. This shows that increasing the superficial gas velocity results in a decrease in the amount of cream, which are the initially present oil droplets in the dispersion. A continuous oil layer was only formed in the columns with a superficial gas velocity of 0.1 and 0.2 cm/s. At 0.5 and 1.0 cm/s, the oil is recovered as a coarse cream layer, which is a layer of oil droplets with a size in the order of millimetres that do not form a continuous oil layer.

Example 4: Effect of Cell Disruption on Batch Oil Recovery

Figure 6:
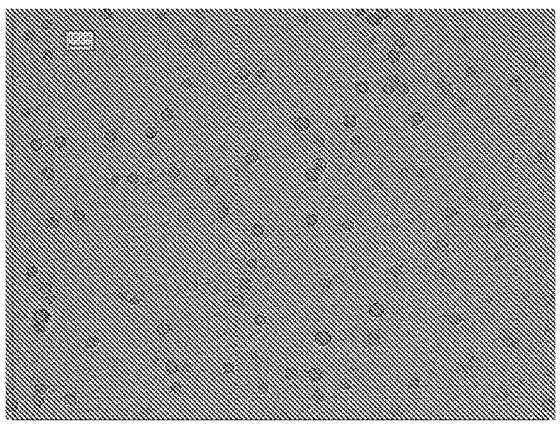
FIG. 6 shows the yeast cells prior to treatment.
Figure 7:
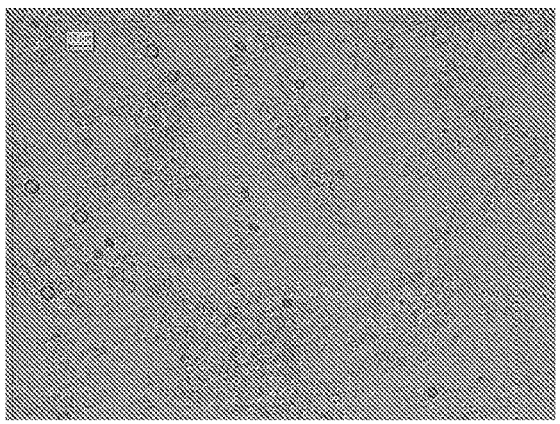
FIG. 7 shows the cell debris suspension that was formed by the treatment.
Figure 8:
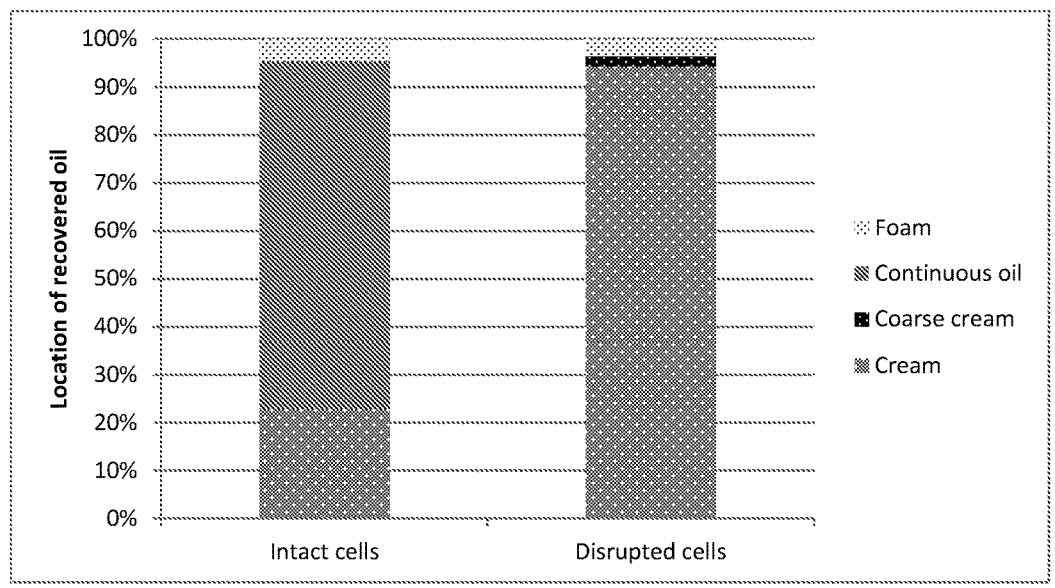
FIG. 8 is a graph showing the effect of cell disruption on batch oil recovery.

Two dispersions were prepared according to the procedure in example 1, with the difference that in one dispersion the aqueous cell suspension was treated with a high pressure cell disruption device (Constant Cell Disruption Systems, Low March, Daventry, Northants) before preparing the dispersion (1 pass at 2.7 kbar). FIG. 6 shows the yeast cells prior to the treatment, as they are used in the preparation of the standard dispersion. FIG. 7 shows the cell debris suspension that was formed by the treatment. With this cell debris, the same dispersion preparation was followed. The prepared dispersion was transferred to similar glass columns as in Example 1 and the separation procedure was carried out for 2 hours at a superficial gas velocity of 0.1 cm/s. Under these conditions, no continuous oil could be recovered as shown in FIG. 8. It can be concluded that the presence of cell debris has a negative effect on separating the product phase from the aqueous phase and in particular the formation of the product layer.

The invention claimed is:

1. Method for recovering a liquid lipid or hydrocarbon from a fermentation mixture, comprising the steps of:
  producing a lipid or hydrocarbon in a fermentation mixture containing living micro-organisms by microbial fermentation in a fermentation vessel or in a first compartment of a fermentation reactor, wherein conditions in the fermentation vessel or in the first compartment of a fermentation reactor are suitable for fermentation, which mixture comprises an aqueous phase and a liquid product phase, wherein the liquid product phase comprises the lipid or hydrocarbon; and wherein the fermentation mixture comprises a substrate; converting, by the living micro-organisms, the substrate into the hydrocarbon or lipid or a mixture thereof, which lipid or hydrocarbon or mixture thereof is then secreted into the fermentation mixture by the living micro-organisms;

feeding at least part of the fermentation mixture to a second vessel or to a second compartment of the fermentation reactor, which part comprises at least part of the aqueous phase and part of the liquid product phase, thereby forming a second mixture; and promoting phase-separation of the aqueous and product phase by injecting a gas into the second mixture, thereby separating the product phase from the aqueous phase and forming a product layer in the second mixture, the product layer having a density greater than 500 kg/m$^3$; and collecting the product layer comprising the lipid or hydrocarbon; and recycling intact micro-organisms present in the second vessel or compartment by feeding them back to the fermentation vessel or first compartment, wherein the second mixture in the second compartment comprises less than 1 wt. % cell debris based on total weight of the second mixture.

2. Method according to claim 1, wherein phase-separation is promoted by controlling the superficial gas velocity of the gas.

3. Method according to claim 2, wherein the gas has a superficial gas velocity in the vessel in the range of 0.01-2 cm/s.

4. Method according to claim 2, wherein at least part of the fermentation mixture or second mixture is subjected to a settling step prior to injecting the gas.

5. Method according to claim 1, wherein phase-separation is promoted by induced gas flotation.

6. Method according to claim 1, wherein the gas is actively fed to the second vessel or second compartment of the fermentation reactor.

7. Method according to claim 1, wherein the gas is a non-oxidizing gas, preferably a gas selected from the group consisting of $CO_2$, inert gas and fermentation gas.

8. Method according to claim 1, wherein the gas is air.

9. Method according to claim 1, wherein besides the lipid or hydrocarbon, a fermentation gas is also produced by microbial fermentation, which fermentation gas is separated from the fermentation mixture and subsequently injected into the second mixture in the step of promoting phase-separation.

10. Method according to claim 1, wherein the gas is distributed through a sparger and/or sintered plate to obtain the desired bubble size and/or flow rate.

11. Method according to claim 1, according to any of the previous claims, wherein the fermentation vessel and second vessel are separate compartments in a fermentation reactor.

12. Method according to claim 11, wherein the fermentation reactor is an gas-lift reactor, which reactor has an internal recirculation or an external recirculation.

13. Method according to claim 1, wherein the microbial fermentation is conducted under aerobic or anaerobic conditions.

14. Method according to claim 1, wherein the lipid or hydrocarbon is produced and separated batch-wise, fed-batch-wise or continuously.

15. Method according to claim 1, wherein a mixture of lipid and hydrocarbon is produced in the microbial fermentation.

16. Method according to claim 1, wherein gas is introduced in the fermentation vessel, wherein the gas has a superficial gas velocity higher than 1.5 cm/s.

17. Method according to claim 1, wherein the promotion of phase-separation results in a product layer having a volume fraction of lipid or hydrocarbon that lies between 0.9 and 1.0.

18. Method according to claim 1, wherein the fermentation vessel comprises a gas outlet for gas bubbles to leave the fermentation vessel, such that gas bubbles introduced or formed in the fermentation mixture do not directly enter the second vessel.

19. Method according to claim 1, wherein the liquid product phase further comprises an organic solvent, in to which the liquid fermentation product is extracted after production by the micro-organisms.

20. Method according to claim 19, wherein the liquid product phase comprises one or more hydrocarbons that are not produced in the microbial fermentation.

21. Method according to claim 1, wherein the second mixture comprises an aqueous layer, a cream layer and a foam layer, wherein the cream layer is an emulsion of the lipid or hydrocarbon in water; and wherein the product layer is formed between the cream layer and the foam layer.

22. Method according to claim 1, wherein the product layer that is collected is a liquid product.

23. Method according to claim 1, wherein said first compartment and said second compartment form part of the same fermentation reactor.

24. Method according to claim 23, wherein the fermentation and the phase-separation occur in the same fermentation reactor such that the lipid or hydrocarbon is produced in said first compartment of the fermentation reactor and said at least part of the fermentation mixture is fed to said second compartment of said fermentation reactor, wherein intact micro-organisms present in the second compartment are recycled by feeding them back to the first compartment.

* * * * *